United States Patent [19]

Davis

[11] Patent Number: 5,022,126

[45] Date of Patent: Jun. 11, 1991

[54] ONE-PIECE PLASTIC TOWEL CLAMP

[75] Inventor: Tommy G. Davis, Athens, Tex.

[73] Assignee: Edward Weck Incorporated, Princeton, N.J.

[21] Appl. No.: 509,940

[22] Filed: Apr. 13, 1990

[51] Int. Cl.⁵ ............................................. A44B 21/00
[52] U.S. Cl. ...................................... 24/543; 24/346
[58] Field of Search ............. 24/543, 339, 346, 16 PB; 606/151

[56] References Cited

U.S. PATENT DOCUMENTS

| | | | |
|---|---|---|---|
| 3,604,071 | 9/1971 | Reimels | 24/543 |
| 3,735,449 | 5/1973 | Rosales | 24/16 PB |
| 3,747,164 | 7/1973 | Fortsch | 24/16 PB |
| 3,982,307 | 9/1976 | Smith et al. | 24/543 |
| 4,212,303 | 7/1980 | Nolan | 24/543 |
| 4,835,824 | 6/1989 | Durham et al. | 24/543 |
| 4,908,911 | 3/1990 | Bretti et al. | 24/16 PB |

Primary Examiner—Victor N. Sakran
Attorney, Agent, or Firm—Gene Warzecha

[57] ABSTRACT

A one-piece molded plastic clamp provided with a guiding lug for engaging a channel to prevent twisting of the arms of the clamp as they are compressed, while simultaneously enabling the clamp to be molded in a simple, clam-shell mold. The clamp includes a pair of parallel toothed members extending inwardly from one arm of the clamp and intended to engage a locking hook extending inwardly from the other of the arms. The teeth on the parallel toothed members are alternatingly spaced so that while the teeth are uniformly spaced within the plane of the clamp, they are staggered within a transverse plane so they unobstructedly face away from the plane of the clamp.

4 Claims, 1 Drawing Sheet

ONE-PIECE PLASTIC TOWEL CLAMP

BACKGROUND OF THE INVENTION

1. Field of the Invention

The invention relates to a clamp and, more particularly, to a one-piece molded plastic clamp suitable for clamping surgical towels, drapes and the like by single-hand, manual operation.

2. Description of the Prior Art

Towel clamps for surgical use are well known and are generally molded in one-piece from various types of moldable resilient plastic material. Known clamps are generally U-shaped and normally open. Because of the resiliency of the material the clamp normally is open except when the arms of the clamp are pressed inwardly and latched in order to press the ends of the arms together.

One type of known, one-piece, plastic towel clamp is described in U.S. Pat. No. 3,604,071 (Reimels). The clamp shown in this patent is a planar U-shaped structure including a pair of parallel toothed members extended inwardly from one arm and a corresponding locking member and guiding lug extending inwardly from the other arm. The toothed members are spaced in a direction transverse to the plane of the clamp to form a channel between the members. The teeth on each toothed member are aligned so two teeth are engaged by the locking member at any one time. The locking member engages the teeth of each of the parallel toothed members as the two arms are pressed together, and the guiding lug slides in the channel to prevent twisting of the arms relative to each other so they will not become disengaged. The disadvantage associated with this particular construction is that it cannot be molded in a simple, clam-shell type mold and, consequently, requires a molding operation which utilizes movable cores or other elements to create the channel between the parallel toothed members.

It is an object of this invention to produce a one-piece plastic clamp having the advantages offered by the aforementioned prior art device but able to be molded in a simple clam-shell type mold without the need for any auxiliary core elements.

SUMMARY OF THE INVENTION

This and other objects of this invention are accomplished by a one-piece, molded, resilient clamp similar to the aforementioned Reimels device, but differing therefrom in that the teeth intended to engage the locking member are staggered so that, when viewed from a point outside the plane of the clamp, any one tooth of one of the parallel toothed members is not directly aligned with a corresponding tooth on the other of the parallel toothed members. Consequently, the teeth of both parallel toothed members are alternatingly engaged by the locking member as the arms are pressed together. In particular, the preferred embodiment is an improvement in a clamp having two substantially straight arms and an arcuately shaped flexible portion connecting the arms, each of the arms having a jaw on the end thereof and the arcuate portion being effective to yieldingly maintain the jaws in a predetermined spaced relationship. A rack having two spaced parallel toothed members extends inwardly from one of the arms with the teeth thereon facing the arcuate portion. A locking member extends inwardly from the other of the arms and has a hook at the end thereof (in alignment with and facing the rack teeth) as well as a guiding lug on the end thereof to pass between the toothed members to maintain alignment between the rack and the locking member and to prevent twisting of the jaws under stress. The hook is adapted to mesh with one of the rack teeth once the jaws are forced inwardly against the pressure of said arcuate portion to thereby maintain the jaws in a clamping relationship. The improvement comprises making the teeth on one of the parallel toothed members staggered relative to the teeth on the other of the parallel toothed members such that the inner surfaces of all teeth unobstructedly face movable in a direction generally transverse to the plane of the clamp. The locking member extends transversely a distance substantially equal to the distance between the outermost faces of the parallel toothed members so that it will engage, at any one time, the teeth of only one of the parallel members.

DESCRIPTION OF THE PREFERRED EMBODIMENT

Figure 1:
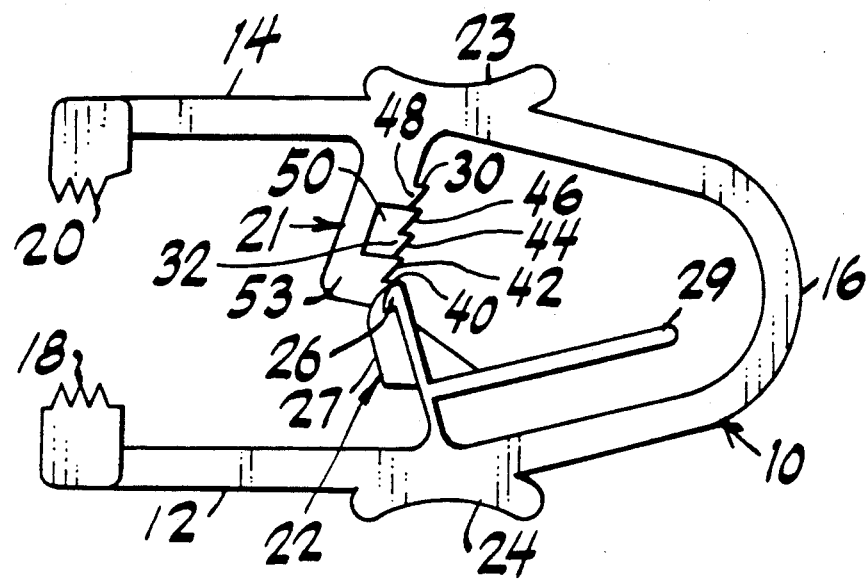
FIG. 1 shows a plan view of a one-piece plastic towel clamp constructed in accordance with the principles of this invention.

Referring to the drawings, there is shown a one-piece plastic towel clamp 10 comprising a pair of arms 12 and 14 joined by a resilient hinge portion 16 and having a pair of facing jaw members 18 and 20 at the free ends of the arms.

The inner ends of arms 12 and 14 are provided with mutually engageable locking means 21 and 22, respectively, and outer thumb and finger engaging pads 23 and 24, respectively. Locking means 22 includes a guiding rib 27 and a transverse hook or tooth 26, the latter being sufficiently wide to overlap both of the rows of parallel toothed members as discussed below.

Figure 2:
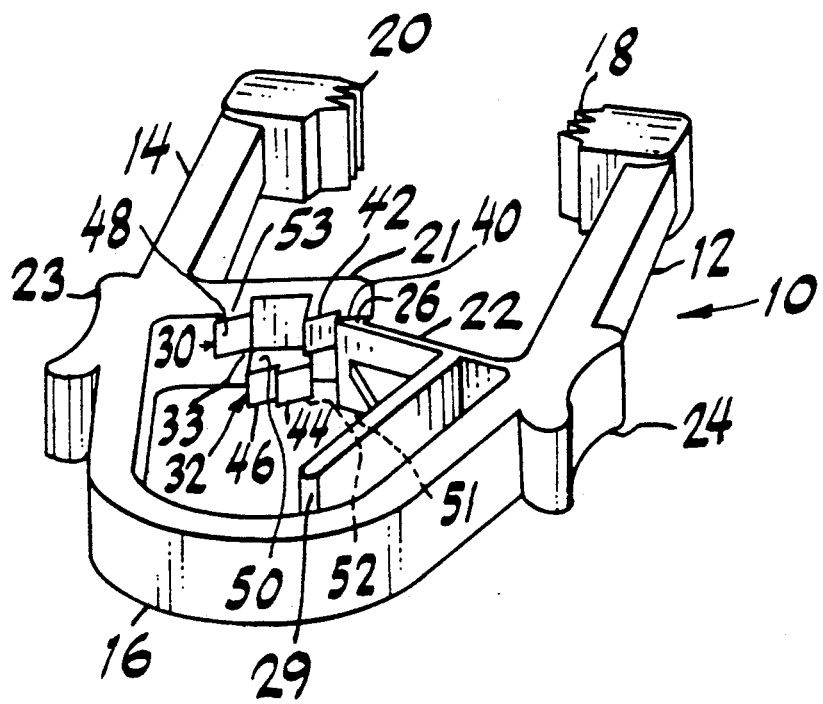
FIG. 2 shows a perspective view of FIG. 1.

Locking means 21 comprises a pair of parallel toothed members 30 and 32, member 30 being a top row or set of teeth and member 32 being a bottom row or set of teeth. As best seen in FIG. 2, sets 30 and 32 are spaced in parallel planes on either side of a separating channel 33. As the arms are pressed together, guiding rib 27 will slide within channel 33. While the teeth of tooth sets 30 and 32 are spaced transversely, it will be understood that as the arms 12 and 14 are pressed together, locking member 26 will engage the teeth of the sets 30 and 32 in an alternating manner depending upon the manner in which teeth are arranged. In the preferred embodiment, locking means 21 is provided with five teeth 40, 42, 44, 46 and 48 which are arranged in alternating pairs so that tooth set 30 has two front teeth 40 and 42 while member 32 is provided with the next two, middle teeth 44 and 46 and member 30 is provided with the final tooth 48. The teeth could be arranged in a single, alternating pattern (not shown) with tooth set 30 having three spaced single teeth 40, 44 and 48 and tooth set 32 having two spaced single teeth 42 and 46. Tooth sets 30 and 32 have inner surfaces 50 and 51 facing channel 37 and outer surfaces 52 and 53 facing away from the clamp. Whichever tooth pattern is chosen to embody the invention, it is important that the inner surfaces 50 and 51 of each tooth will always be unobstructedly visible from a point above (or below) the plane of the clamp, as best seen in FIG. 1. The teeth 40-48 are uniformly spaced along locking means 21 (i.e. within the plane of the clamp) so a user will not sense the gap between the teeth but will merely feel a uniform ratcheting action as arms 12 and 14 are pressed together and tooth 26 latches one tooth after another. It is noted the tooth 26 is wide enough to engage teeth on either set 30 or 32, and in the preferred embodiment the outer surfaces of tooth 26 are parallel to outer surfaces 52 and 53.

In order to enable the operation of guiding rib 27 throughout the range of motion of arms 12 and 14, it is necessary that the rib be longer than the length of the gap between any two consecutive teeth o either set 30 or 32. Obviously, if there is an innermost area on any set that is devoid of teeth (e.g. beyond tooth 48) rib 27 must be long enough to prevent tooth 26 from twisting out of this area.

It will be understood by those skilled in the art that numerous improvements and modifications may be made to the preferred embodiment of the invention disclosed herein without departing from the spirit and scope thereof.

What is claimed is:

1. In a one-piece, molded, resilient towel clamp having two substantially straight arms and an arcuately shaped flexible portion connecting said arms, each of said arms having a jaw on the end thereof and said arcuate portion being effective to yieldingly maintain said jaws in a predetermined spaced relationship, a rack having two spaced parallel toothed members extending inwardly from one of said arms with the teeth thereon facing said arcuate portion, a locking member extending inwardly from the other of said arms and having a hook at the end thereof in alignment with and facing said rack teeth and having a guiding lug on the end thereof positioned to pass between said toothed members to maintain alignment between said rack and said locking member and to prevent twisting of said jaws under stress, said hook being adapted to mesh with one of said rack teeth once the jaws are forced inwardly against the pressure of said arcuate portion to thereby maintain said jaws in a clamping relationship, the improvement comprising:

the teeth on one of said parallel toothed members being alternatingly disposed relative to the teeth on the other of said parallel toothed members such that the inner surfaces of all teeth unobstructedly face in a direction generally transverse to the plane of said clamp, said locking member extending transversely a distance substantially equal to the distance between the outer surfaces of said teeth such that said locking member will engage, at any one time, the teeth of only one of said parallel members.

2. The improvement according to claim 1 wherein said guiding lug is sufficiently long to overlap both consecutive teeth on either of said parallel members.

3. The improvement according to claim 1 wherein said teeth are spaced along said parallel toothed members such that, upon inward movement of said jaws, said locking member first engages at least one tooth on one of said parallel toothed members and then disengages all teeth on such parallel toothed member and engages at least one tooth on the other of said parallel toothed members.

4. The improvement according to claim 3 wherein said one of said parallel toothed members is provided with at least one additional tooth such that it may be engaged by said locking member upon inward movement thereof past, and disengagement from the last tooth on said other parallel toothed member.

* * * * *